United States Patent [19]

Barberet et al.

[11] Patent Number: Plant 6,711

[45] Date of Patent: Apr. 4, 1989

[54] CARNATION NAMED LONTEREY

[75] Inventors: Nicole Barberet; Yves Ducloux, both of Antibes, France

[73] Assignee: Laboratoire de Physiologie Vegetale de la Londe, La Londe, France

[21] Appl. No.: 100,720

[22] Filed: Sep. 24, 1987

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new carnation cultivar particularly distinguished by the light pink coloration of its medium sized, relatively dense and almost ball-shaped blooms, which are borne on long, straight, strong stems of a plant which blooms profusely and recurrently from spring through midseason and fall with a vigorous, upright growth habit and with moderately abundant foliage, the plant averaging about 112 cm. in height and thereby providing the flowers with extra long stems particularly suitable for the cut flower market.

1 Drawing Sheet

BACKGROUND OF THE NEW PLANT

This new carnation cultivar originated at La Londe, Les Maures, France, as a sport of the variety 'Londaxie' (U.S. Plant Pat. No. 5,530) and was selected for propagation because of its unique and uniform coloration in a well-shaped flower having numerous and rather densely arranged petalage and being carried on long, strong an rather rigid stems. The selected plant was reproduced under our direction at La Fonde, France, by means of cuttings, with very favorable results and continued propagation through several successive generations demonstrated clearly that the novel and distinctive characteristics of the new plant appeared to be firmly fixed and would be retained by asexual propagation from generation to generation.

DESCRIPTION OF THE DRAWING

Our new carnation cultivar is illustrated by the accompanying photographic drawing which shows, in full color, a group of flowering stems showing buds and blooms in various stages of opening to a fully matured flower, thereby illustrating the flowering characteristics of the plant and the nature of its foliage, the colors shown being as nearly true to that specified herein as is reasonably possible to obtain by professional photographic procedures.

DESCRIPTION OF THE NEW PLANT

The following is a detailed description of our new carnation cultivar based upon observations of greenhouse grown plants made at La Londe, Les Maures, France, the color designations being specified according to the R.H.S. Colour Chart published by The Royal Horticultural Society of London, England.

THE PLANT

Origin: Sport.

Parentage: The variety 'Londaxie' (U.S. Plant Pat. No. 5,530).

Classification:

*Botanic.*—*Dianthus caryophyllus.*

*Commercial.*—Standard Carnation.

Form: Tall, erect bush comprising at least four stems emitted near the ground as the result of pinching of the main stem at about 15 cm., the stems reaching a height averaging about 112 cm. at 8 months of growth.

Growth habit: Vigorous, upright, strong and rather rigid.

Foliage:

*Quantity.*—Moderately abundant.

*Number of leaves.*—More than 120.

*Leaf size, at the 7th node.*—About 12.9 cm. long and 0.9 cm. wide with rolled margins.

*Texture.*—Leathery.

*Color.*—Both upper and under sides, 189-A.

*Ribs and veins.*—Hardly noticeable.

THE BUD

Form: Short, cylindrical and urn-shaped.

Color of petals: When sepals first divide and when petals begin to unfurl, between 49-B and 50-C.

Sepals:

*Number.*—Five (exceptionally six).

*Shape.*—Mucronate and joined together at the lower part.

*Character.*—Hooded over the bud and standing up as the flower opens.

*Color.*—Inside, Greenish White. Outside, 189-C.

Calyx:

*Shape.*—Bell-shaped.

*Size.*—Large, broad and of medium length.

*Aspect.*—Smooth.

*Splitting.*—The calyx does not split.

Flower stem:

*Length.*—About 77 cm., in average, when cut at the tenth node.

*Character.*—Erect and rather rigid.

*Color.*—189-A, B.

THE FLOWER

Blooming habit: Recurrent and profusely from spring through fall with a tendency to give few blooms in the fall.

Flower size: Medium.

*Diameter.*—About 8.9 cm.

*Depth.*—About 6.5 cm.

Borne: Singly.

Shape:

*When bloom first opens.*—High centered.

*When bloom matures.*—Ball-shaped.

Petalage:

*Number of petals.*—66 to 81 (67, in average).

*Arrangement.*—Imbricated.

*Form.*—Fan-shaped with rounded edges and serrated apex.

*Texture.*—Soft.

*Appearance.*—Satiny.

*Color.*—All petals: Upper side body — Between 49-B and 50-C with a greenish base. Reverse side — 50-C.

Petaloids:

*Size.*—Smaller than petals.

*Color.*—The same as the petals.

Discoloration after full bloom: Ratherf weak.

Persistence: The flowers hang on and dry.

Fragrance: Perceptible.

Disease resistance: Rather resistant to *Fusarium oxysporum* as observed INRA-Antibes-France.

Lasting quality:

*As a cut flower.*—At least ten days in vase keeping.

REPRODUCTIVE ORGANS

Stamens:

Number.—8 to 19.

*Arrangement.*—Around the ovary.

*Anthers.*—Size: Less than 0.4 cm. Color: Whitish.

Pistils:

*Number.*—4 to 6 with white styles.

Character of ovary: The ovary is ribbed.

Compared with the variety 'Londaxie', this new plant has a bloom of paler color and with no defect in the outer petals.

We claim:

1. The new and distinct carnation cultivar and parts thereof, substantially as herein shown and described, characterized by the uniform overall pink coloration of its medium sized, ball-shaped blooms which are carried on long, straight, strong and rigid stems, and by its vigorous growth habit with a moderately abundant production of foliage.

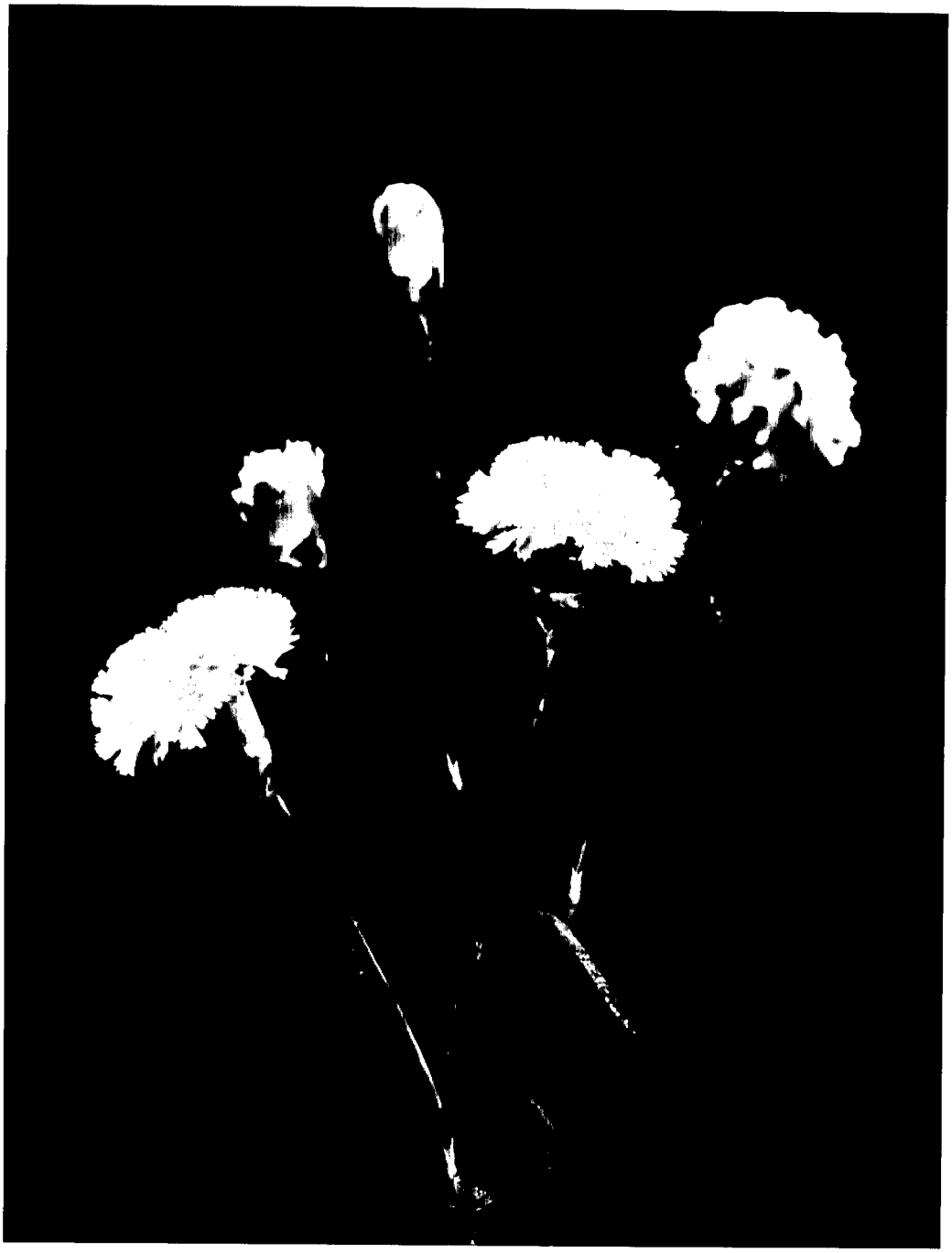

* * * * *